United States Patent [19]

Crostack

[11] Patent Number: 4,531,410
[45] Date of Patent: Jul. 30, 1985

[54] METHOD OF AND APPARATUS FOR DETECTING FLAWS INSIDE ARTICLES, MORE PARTICULARLY STRUCTURAL COMPONENTS, BY MEANS OF ACOUSTIC HOLOGRAPHY

[76] Inventor: Horst-Artur Crostack, Beringweg 2, 5860 Iserlohn, Fed. Rep. of Germany

[21] Appl. No.: 492,414

[22] Filed: May 6, 1983

[30] Foreign Application Priority Data

May 10, 1982 [DE] Fed. Rep. of Germany ....... 3217530
May 10, 1982 [DE] Fed. Rep. of Germany ... 8213515[U]

[51] Int. Cl.³ ............................................ G01N 29/04
[52] U.S. Cl. ..................................................... 73/603
[58] Field of Search ................. 73/603, 598, 600, 606, 73/625, 627; 367/8

[56] References Cited

U.S. PATENT DOCUMENTS 3,250,120  5/1966  Dickinson .............................. 73/627
3,540,267 11/1970  Wood ..................................... 73/625
4,179,936 12/1979  Bennett et al. ........................ 73/606

FOREIGN PATENT DOCUMENTS 2827489 of 0000 Fed. Rep. of Germany.
1251713 of 0000 United Kingdom.

OTHER PUBLICATIONS

Materialprüfung 22, No. 12, S. 465–470.
Krautkramer "Werkstoffprüfung mit U.S.", 1975, S. 184–189.
Proc. of the I.E.E., No. 9, Sep. 1971 S. 1319–1334.
Kiemle/Ross: "Einführung in die Technik der Holographie, Akademische Verlagsgesellschaft Frankfurt a. Main 1969 S. 245–248.
"British Journal of NDT", vol. 21, No. 4, Jul. 1979, pp. 212–213, A New Technique for Ultrasonic Imaging" by Hanstead.

Primary Examiner—James J. Gill
Attorney, Agent, or Firm—Toren, McGeady, Stanger, Goldberg & Kiel

[57] ABSTRACT

In a method of and an apparatus for detecting flaws inside articles, the flaw area for detection being subjected to ultrasonic pulses on which, after reaction with the flaw, a reference beam is superimposed, whereupon the resulting interference field is holographically detected, reconstructed and evaluated. This method can be applied to thin and sound-scattering materials with improved resolution and a description of the flaw configuration and detection of the deformation behavior of flaws. In the method, a load is applied to the flaw area under investigation and this area is subjected to ultrasonic pulses at least at two different times each corresponding to an extreme value of the loading, the ultrasonic pulses being short with respect to the load period and, after reaction with the flaw, reference pulses are superimposed on the ultrasonic pulses, whereupon the holograms of these ultrasonic applications are superimposed to give an interferogram which can be evaluated. The block schematic diagram of an apparatus for performing the method is shown in FIG. 1, in which reference 1 denotes a loading unit, 3 an ultrasonic transmitter and the units 11–5 form a control unit.

9 Claims, 5 Drawing Figures

METHOD OF AND APPARATUS FOR DETECTING FLAWS INSIDE ARTICLES, MORE PARTICULARLY STRUCTURAL COMPONENTS, BY MEANS OF ACOUSTIC HOLOGRAPHY

This invention relates to a method of detecting flaws inside articles, more particularly structural components, by acoustic holography, in which the flaw area to be detected is subjected to ultrasonic pulses on which, after reaction with the flaw, a reference beam is superimposed, whereupon the resulting interference field is holographically detected, reconstructed and evaluated.

The invention also relates to apparatus for performing this method, comprising an ultrasonic transmitter for generating and triggering the flaw and reference pulses, a receiver for the sound and for the interference field from the testpiece, and units for producing, reconstruction and evaluation of the holograms.

The main field of application of the invention is the testing and monitoring of structural components and machinery, apparatus and the like for damage, and any progressive development of such faulty areas. However, the invention can also be applied to any other field in which the movement or deformation of an area within a body is to be determined by nondestructive testing.

Acoustic holography is extremely important in nondestructive testing, particularly for describing flaws inside structural components, since with it it is possible to represent the area in question three-dimensionally.

For this purpose ultrasonics are applied to the component under test. After the ultrasonic have reacted with the flaw area, there is a superimposition with a reference beam which produces an interference which is amplitude and phase dependent. This interference field is retained in the form of a hologram and reproduces the flaw picture in the subsequent reconstruction, which can be produced either mathematically or optically.

The known methods and apparatus used in acoustic holography have the following disadvantages:

It is not possible to test thin components. Due to the shape of the ultrasonic pulses, which are usually cyclic sinusoidal oscillations, the pulse is too large with the coherence length required.

It is not possible to test materials which scatter sound, because the pulse length results in a relatively wideband spectrum and there is accordingly separation in sound-attenuating materials and this changes the composition of the pulses and hence destroys the coherence.

The resolution is limited to the wavelength even under favourable conditions. Difficulties arise even with easily tested materials because the resolution for the flaw contour drops with increasing aperture length. Owing to the pulse length, the distance is relatively considerable, however, and the aperture length is small with the scanning operation usually carried out (this is time-consuming and entails difficulties in respect of coupling, particularly in the case of components having complicated geometry and technically rough surfaces).

Another considerable disadvantage with this type of holography due not least to this reason is that only the absolute picture of the flaw can be sensitively measured and not its change or deformation. Although it is possible in this way to obtain a description of the flaw, it is not possible to detect its criticality. Analysis of the flaw risk requires not only the flaw geometry but also the toughness or state of deformation of the material at the flaw site. It is not possible to obtain any information on this with the known apparatus and methods.

The object of the invention is to provide a method and apparatus which not only provides improved resolution and description of the flaw configuration but also enable the deformation behaviour of flaws to be detected and which can also be applied to thin materials and those which scatter sound.

The method according to the invention is characterised in that a load is applied to the flaw area and this area is subjected to ultrasonic pulses at least at two different times of the loading (minimum and maximum in the case of cyclic loading, before the loading and at maximum loading in the case of single loading), said ultrasonic pulses being short with respect to the period of the loading and, after reaction with the flaw, reference pulses are superimposed on said ultrasonic pulses, whereupon the holograms of these sonic applications to the flaw are superimposed to form an interferogram which can be evaluated.

Other features of the invention are indicated in the subclaims, more particularly the construction of the apparatus for performing this method.

The invention is illustrated and explained hereinbelow with reference to the drawings wherein.

The invention is based on the idea of determining the deformation properties of the material, and particularly the elastic-plastic transitions and any enlargement in the area of the flaw by detecting the deformation behaviour of the flaw under a test load by means of acoustic interferometry.

Figure 1:
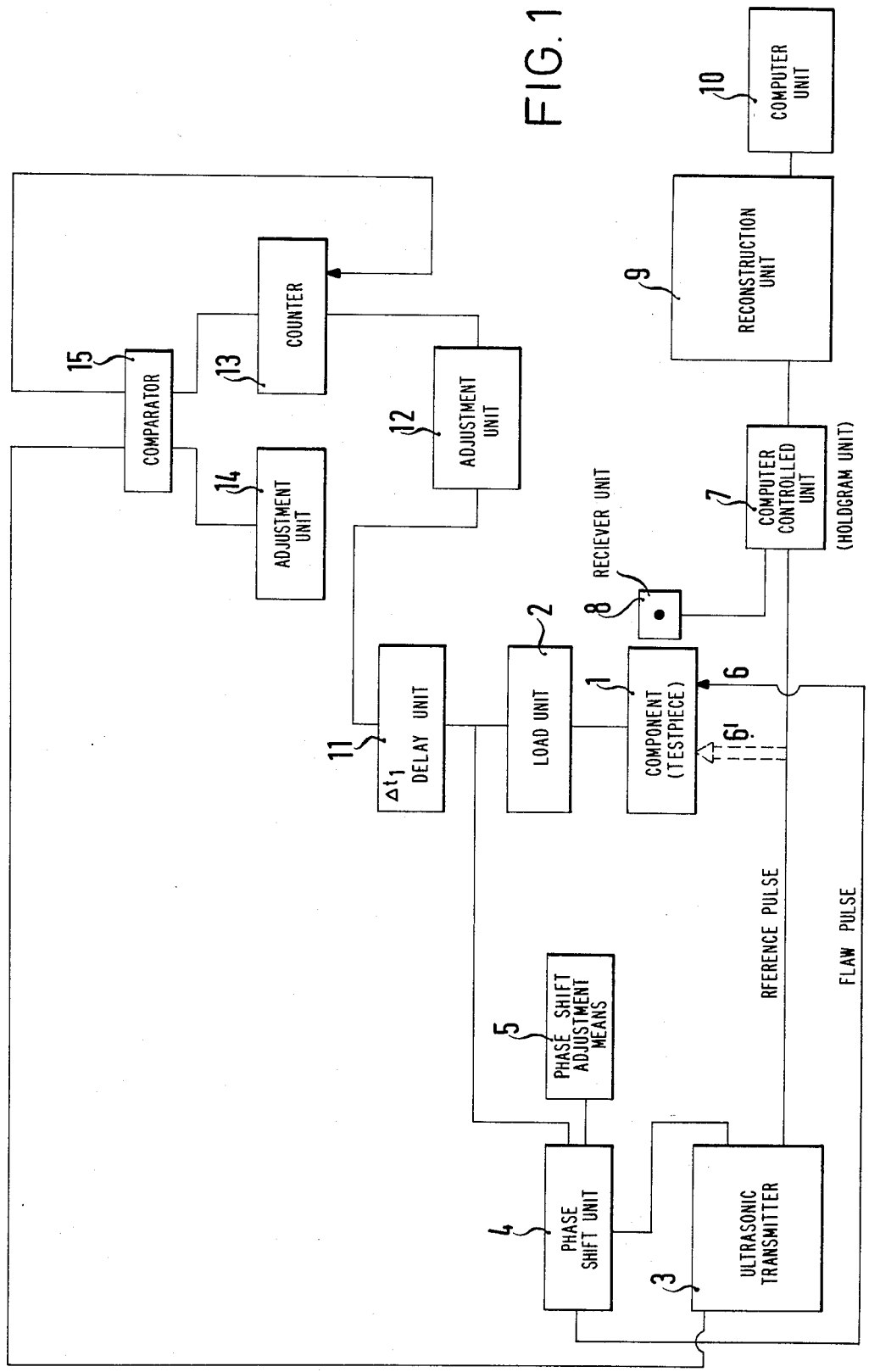
FIG. 1 is a block schematic of the apparatus for performing the method.
Figure 2:
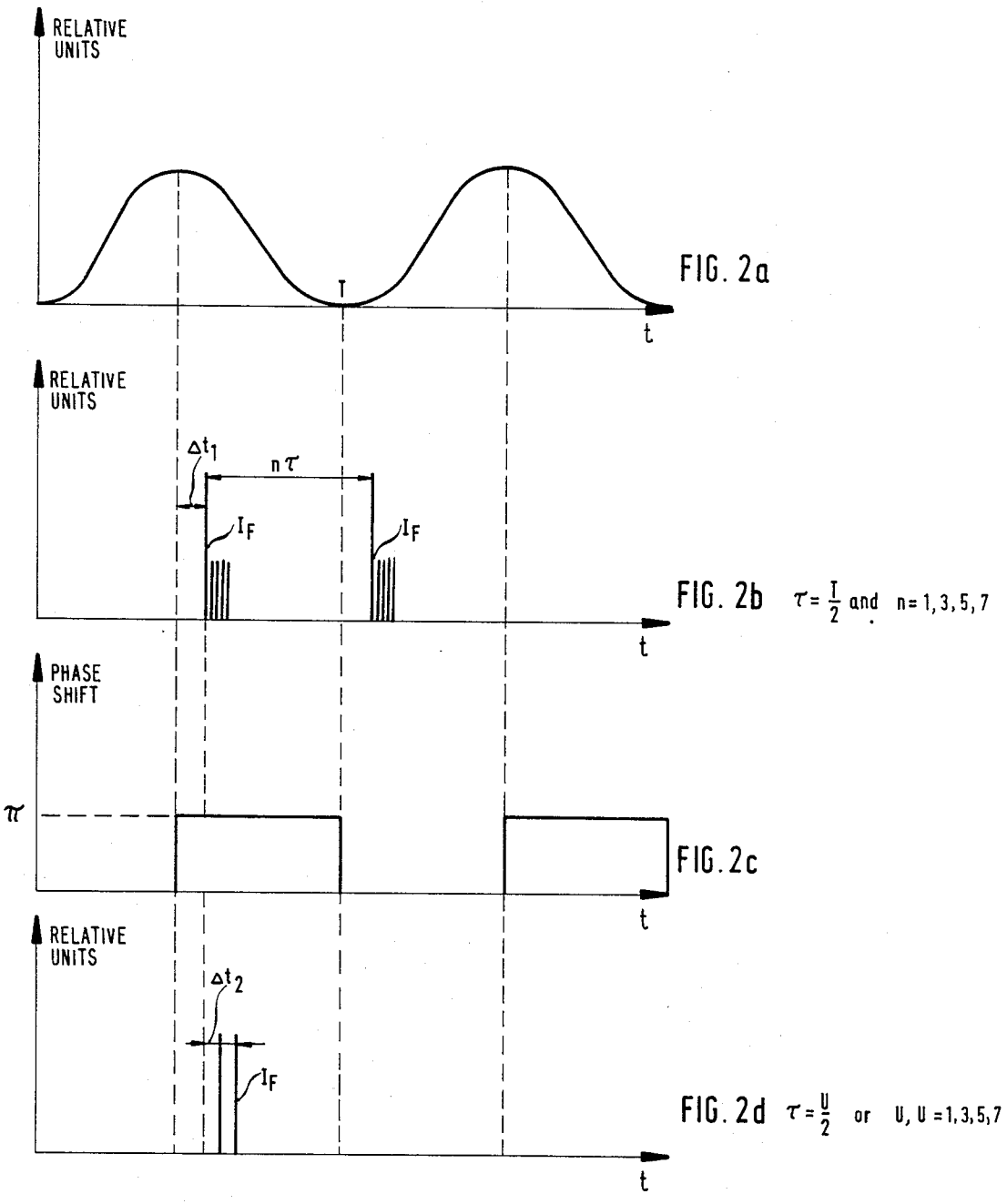
FIG. 2 is an explanatory sketch showing the principle of the method.

Referring to FIG. 1, a component having a flaw for detection in its interior is denoted by reference 1. A load unit 2 applies a test load either mechanically or electromagnetically or thermally to the testpiece 1 either as an individual load or cyclically. FIG. 2a of FIG. 2 shows the curve for a cyclically applied test load of period T. An ultrasonic transmitter 3 is provided to generate the ultrasonic pulses for application to the flaw area (flaw pulses $I_F$) and the reference pulses $I_R$ which are to be superimposed on the flaw pulses in order to form holograms. The ultrasonic pulses (flaw pulses $I_F$) generated by the transmitter 3 are of short duration compared with the duration or period of the load and are optimized in respect of the test head and workpiece properties. The relative phase between each flaw pulse $I_F$ and the corresponding reference pulse $I_R$ is switched, between the two flaw pulses $I_F$, by a preselected amount which may be $\pi$ or a different value. Also, if required, a new interferogram having an offset phase can be superimposed. In this way the measurement is adapted to the acoustic noise due to the flaw surface, the material structure and the workpiece surface, and the noise is also reduced. The sensitivity can be increased by the fact that deformation situated far below the wavelength of the ultrasonic signal used, e.g. amounting to one-thousandth thereof, can be detected. The wavelength of the ultrasonic signal is generally in the millimeter range. Deformations or extensions of this dimension are not likely in the case of small flaws.

To provide this phase shift between each two flaw signals, the load unit 2 in synchronism with the loading controls a phase shift unit 4 which is adjustable by an adjustment means 5 in respect of the amount of the phase shift. Unit 4 modulates the phase of the flaw pulse $I_F$ provided by the ultrasonic transmitter 3 before it is introduced via a testhead 6 into the testpiece 1 under investigation. The phase shift and hence the relative phase between the flaw pulse $I_F$ and the reference pulse $I_R$ is shown in FIG. 2c in FIG. 2. The amount of phase shift is adapted to the acoustic noise.

The reference pulse $I_R$ is also introduced by test head 6' into the testpiece 1, where it is superimposed on the flaw pulse $I_F$ to form an interference field or else, if it is of a purely electrical nature, the flaw pulse is first received from the testpiece 1 in a computer-controlled unit 7 while the reference pulse is input directly to the unit 7 where it is superimposed with the flaw pulse $I_F$ to form the hologram. A receiver unit 8, which may be an ultrasonic testhead or an interferometry unit is provided to receive either the flaw pulse $I_F$ after it has reacted with the flaw, or the interference field resulting from superimposition of the flaw pulse $I_F$ and the reference pulse $I_R$ in the testpiece 1. FIG. 2d of FIG. 2 shows the time of the optical sonic field reception, $\Delta t_2$ denoting the transit time of the ultrasonic pulse from the flaw to the testpiece surface and U the period of the ultrasonic oscillation. $\tau$ is the interval of time between two load values governing the ultrasonic application times, either between the extreme values of the loading or between intermediate loading values.

The ultrasonic pulse is also triggered by means of the loading unit 2 via a delay unit 11 which delays the control signal from the loading unit by a predetermined amount $\Delta t_1$, which is equal to the interval of time during which the load has advanced from the surface of the testpiece to the location of the flaw. The load signal delayed in this way is fed to an adjustment unit 12 for the time interval $\tau$, and this selectively records either just the extreme values of the loading or intermediate values thereof and feeds the same to a counter 13 which records the number of time intervals $\tau$ elapsing. The output of counter 13 is connected to the input of a comparator 15 in parallel to an adjustment unit 14 for the number n of time intervals $\tau$ required to give the interval of time between two sonic applications. When the number of intervals $\tau$ recorded by the counter agrees with the number n preset by the unit 14, comparator 15 delivers a pulse which triggers the ultrasonic transmitter 3 and the ultrasonic pulse. The time sequence described above is illustrated in FIG. 2b of FIG. 2 for $\tau = T/2$ (T = period of oscillation) and n = 1, 3, 5, 7. Simultaneously with the ultrasonic pulse triggering the counter 13 is re-zeroed and reset.

The holograms of the two sonic applications to the flaw are optically reconstructed and superimposed in a reconstruction unit 9 either mathematically or after conversion (reduction based on wavelength differences). The resulting interferogram is evaluated in a computer unit 10 in respect of its streak configuration (streak curve, streak distances etc) and the resulting information is converted to the movements or deformations of the flaw.

To ensure that the flaw location has the coherence required for holography in materials having a highly attenuating effect on sound, or thin-walled components, the transmission pulse for the investigation of such components or materials is so devised that the transmission properties of the material are allowed for so that, for example, it is possible to use pulses with similarity criteria or image functions. This is effected by analyzing a test pulse, the variation of which is measured and superimposed as a correction on the transmission pulse, which already has the required coherence.

The apparatus and method according to the invention allows the detection of even small movements and deformations of flaws, and their first enlargement when still not critical for the testpiece. In these conditions the sensitivity can be so increased as to detect movements which are just a fraction of a wavelength. In order further to reduce noise, it is also possible subsequently to carry out negative superimposition of two interferograms which cover the same object but which are offset in phase.

If the loading remains unchanged and instead the location at which the ultrasonic pulses are applied or the test frequency is changed between the pulses in the case of interferometry, the contour of the flaw can be distinguished in the form of altitude or contour lines. The result is an interferogram which reacts sensitively to the frequency change or angle change and which in addition to lateral extension also allows direct viewing of the depth extension.

The main criteria for the technical advance provided by the invention are as follows:

It is not only the flaw itself, but also its movement and deformation that are detected. In this way it is possible to estimate the flaw criticality.

The flaw deformation is determined directly at the flaw and hence independently of flaw depth.

Any propagation of a crack can immediately be detected both in respect of direction and dimensions.

Areas of different deformability are detected according to the type of excitation.

It is possible to carry out the test with guided waves, since the pulse length is not important in interferometry.

With optical reception of the interference field the accuracy of reproduction of the deformation picture is increased as a result of the large aperture and more accurate reception.

The influence of acoustic noise (shape of flaw and workpiece surface) can be reduced by phase shifting, thus giving increased sensitivity.

The high increase in sensitivity enables extremely small movements to be detected so that it is also possible to assess flaw areas in materials having a high modulus of elasticity.

I claim:

1. A method of detecting flaws inside articles, such as structural components, by acoustic holography, in which the flaw area to be detected is subjected to ultrasonic pulses on which, after reaction with the flaw, a reference beam is superimposed, whereupon the resulting interference field is holographically detected, reconstructed and evaluated, characterized by applying a load to the flaw area and subjecting the flaw area to ultrasonic pulses at least at two different times of the loading (minimum and maximum in the case of cyclic loading, before the loading and at maximum loading in the case of single loading), the ultrasonic pulses being short with respect to the period of the loading and, after reaction with the flaw, superimposing reference pulses ($I_R$) on said ultrasonic pulses, changing the relative phase between the flaw pulse ($I_F$) and the reference pulse ($I_R$) by a predetermined amount between the individual sonic applications to the loaded flaw whereupon superimposing the holograms of these sonic applications to the flaw to form an interferogram which can be evaluated.

2. A method according to claim 1, characterised by superimposing two interferograms of different phases.

3. A method, according to claim 1, characterised by changing the carrier frequency between each two flaw pulses ($I_F$).

4. A method, according to claim 1, characterised by changing the distance (angle) of the testhead applying the ultrasonic pulses between each two flaw pulses.

5. Apparatus for detecting flaws inside articles, such as structural components, by acoustic holography, comprising a first unit (3) including an ultrasonic transmitter for generating triggering ultrasonic flaw pulses ($I_F$) and one of ultrasonic and electrical reference pulses ($I_R$), at least one test head (6, 6') connected to said first unit (3) for directing a flaw pulse ($I_F$) or a flaw pulse ($I_F$) and a reference pulse ($I_R$) into the flaw area of a test piece (1), a receiver (8) for the sound field of the flaw pulse ($I_F$) or the interference field of the flaw and reference pulse ($I_F+I_R$) from the test piece (1), and a second unit (7) connected to said receiver (8) for producing holograms of the interference field, which in the case of a purely electrical reference pulse ($I_R$), comprises means for superimposing this electrical reference pulse ($I_R$) and the flaw pulse ($I_F$) after reaction of the latter with the flaw, characterized by a loading unit (2) arranged for applying a load to the test piece (1) the duration or period of which is long compared with the duration of the flaw pulse ($I_F$) and controls a control unit (11–15) connected to said first unit (3) for delivering the signal triggering said transmitter of said first unit (3) whenever the loading of the flaw reaches a predetermined extreme value (minimum and maximum in the case of cyclic loading, before the loading and at the maximum loading in the case of a single loading), said loading unit connected to said control unit, a third unit (4) connected to and controlled by the loading unit (2) for changing the relative phase between the flaw pulse ($I_F$) and the reference pulse ($I_R$) by a predetermined adjustable amount simultaneously with the sonic applications to the loaded flaw, and a fourth unit (9) connected to said second unit (7) for reconstructing and superimposing the holograms of the sonic applications to the flaw to form an interferogram, and an evaluator (10) connected to said fourth unit (9) for evaluating the interferogram.

6. Apparatus according to claim 5, wherein said control unit (11–15) includes a delay unit (11) by means of which the signal coming from the loading unit (2) for triggering the ultrasonic transmitter (3) is delayed by a preselectable amount $\Delta t_1$.

7. Apparatus according to claim 5, wherein said control unit (11–15) for triggering the ultrasonic transmitter (3) comprises an adjustment unit (12) for counting the extreme values or intermediate values of the loading, and a counter (13) which follows said adjustment unit (12), a comparator (15) having an input, an adjustment unit (14) arranged parallel to said counter (13) in said control unit (11–15) and connected to said comparator (15), said counter (13) is connected to the input of said comparator (15) for adjusting the interval of time between two ultrasonic applications, said comparator (15) delivers a pulse triggering the ultrasonic transmitter (3) when the values counted by the counter (13) give a time interval corresponding to the time between two ultrasonic applications.

8. Apparatus according to claim 5, including a selector means for the carrier frequency for the unltrasonic transmitter (3).

9. Apparatus according to claim 5, including a selector means for the distance (angle) of the ultrasonic test head (6, 6').

* * * * *